United States Patent [19]

Bennett et al.

[11] 4,418,224

[45] Nov. 29, 1983

[54] PREPARATION OF ORTHO-ALKYLATED PHENOLS USING MAGNESIUM COMPOUND CATALYSTS

[75] Inventors: James G. Bennett, Delmar, N.Y.; Freddie L. Tungate, Georgetown, Ind.

[73] Assignee: General Electric Company, Pittsfield, Mass.

[21] Appl. No.: 303,567

[22] Filed: Sep. 18, 1981

[51] Int. Cl.$^3$ .............................................. C07C 37/16
[52] U.S. Cl. ................................... 568/804; 568/794
[58] Field of Search ........................ 568/804, 794, 789

[56] References Cited

U.S. PATENT DOCUMENTS

| | | | |
|---|---|---|---|
| 3,446,856 | 5/1969 | Hamilton | 568/747 |
| 3,843,606 | 10/1974 | van Sorge | 568/804 |
| 3,873,628 | 3/1975 | van Sorge | 568/804 |
| 3,968,172 | 7/1976 | Ichikawa et al. | 568/804 |
| 3,971,832 | 7/1976 | Watanabe et al. | 568/804 |
| 3,972,836 | 8/1976 | van Sorge | 568/804 |
| 3,974,229 | 8/1976 | van Sorge | 568/804 |
| 3,974,229 | 8/1976 | van Sorge | 568/804 |
| 4,041,085 | 8/1977 | Frabetti | 568/804 |
| 4,100,207 | 1/1978 | Goodwin et al. | 568/804 |
| 4,201,880 | 5/1980 | van Sorge | 568/804 |

FOREIGN PATENT DOCUMENTS 907065  8/1972  Canada ................................ 568/804

*Primary Examiner*—Werren B. Lone
*Attorney, Agent, or Firm*—Hedman, Casella, Gibson, Costigan & Hoare

[57] ABSTRACT

Ortho-alkylated phenols are prepared by reacting phenol unsubstituted in at least one ortho position with an alcohol in the presence of an ortho-alkylation catalyst consisting of magnesium carbonate, magnesium hydroxide or a mixture of both. The catalyst is used in the absence of a promoter compound and with or without polymeric binder.

24 Claims, No Drawings

PREPARATION OF ORTHO-ALKYLATED PHENOLS USING MAGNESIUM COMPOUND CATALYSTS

BACKGROUND OF THE INVENTION

Methods for the alkylation of the ortho position of phenols having at least one ortho-hydrogen are known in the art. Such methods are usually carried out in the presence of a catalyst.

Hamilton, U.S. Pat. No. 3,446,856 discloses a method for methylating the ortho positions of phenol by the vapor phase reaction of a phenol with methanol in the presence of magnesium oxide at a temperature in the range of 475° to 600° C.

Van Sorge, U.S. Pat. No. 3,873,628, discloses a method for the ortho-alkylation of phenol in the presence of a catalyst consisting of a mixture of magnesium oxide and manganese sulfate.

Other Van Sorge patents describe methods for the ortho-alkylation of phenols using a magnesium oxide catalyst together with a "promoter" consisting of manganese oxide (U.S. Pat. No. 3,974,229), or a magnesium oxide catalyst bonded with an inert organic cellulose polymeric binder (U.S. Pat. No. 3,972,828).

It is desirable to carry out the ortho-alkylation of phenols in the presence of a catalyst which does not depend on the use of a promoter compound or polymeric binders for the catalyst. The procedure described in the aforementioned Hamilton patent, using magnesium oxide alone serves the purpose to some extent. However, it is known that in Hamilton's procedure the service life of the magnesium oxide catalyst is relatively short because of the high temperatures required, 475° to 600°., and there is only moderate selectivity with respect to methanol.

INTRODUCTION TO THE INVENTION

It has now been discovered that the ortho-alkylation of phenols in the vapor phase can be carried out in the presence of a catalyst from the group consisting of magnesium carbonate, magnesium hydroxide and mixtures of the two, to produce the ortho-substituted phenol in high yields. This reaction proceeds at lower temperatures than permitted by many prior art processes, without a reduction in selectivity to the desired ortho-alkylated end product.

In carrying out the process of the invention, it is desirable to conduct the reaction at a temperature of at least 400° C., with temperatures in the range 400° to 460° C. being preferred.

The magnesium carbonate and/or magnesium hydroxide catalyst is employed in the process of the invention without a promoter and with or without polymeric binders.

By the term "magnesium carbonate" there is meant those compounds having the formula MgCO₃, as well as those compounds known as "basic" or "light" magnesium carbonates, e.g., having the formula 4MgCO₃.Mg(OH)₂.5H₂O.

DESCRIPTION OF THE INVENTION

According to this invention, ortho alkylated phenols are formed by a process which comprises the vapor phase reaction of an alkyl alcohol and a phenol having at least one unsubstituted ortho position, in the presence of a catalyst from the group consisting of magnesium carbonate, magnesium hydroxide or a mixture of the two, at a temperature of at least 400° C. and preferably between 400° and 460° C.

Examples of the alcohols include saturated aliphatic alcohol such as methyl, ethyl, propyl, isopropyl, butyl, isobutyl, tert-butyl, amyl, isoamyl, hexyl, heptyl, octyl, nonyl, decyl, lauryl, cetyl, cyclohexyl, and the like; alcohols, especially alcohols having up to 6 carbon atoms, and most preferably, methanol.

The invention is described with reference specifically to phenols and ortho-cresol. It can be applied in general to any phenol having an ortho-hydrogen, however. For instance, the process can be used with ortho-phenyl phenol, ortho-ethyl phenol, and phenols in which there are alkyl and aryl groups in the meta- and para-positions. These phenols can be represented by the formula:

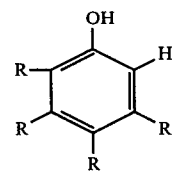

where each R is a monovalent substituent selected from the group consisting of hydrogen, alkyl, e.g., $C_1-C_{12}$ alkyl, phenyl and alkyl-substituted phenyl, e.g., $C_1-C_{12}$ alkyl-substituted phenyl.

In carrying out an alkylation in accordance with this invention, any one or a mixture of phenols having an ortho hydrogen is vaporized and passed through a reactor heated to a temperature of at least 400° C. and containing the magnesium carbonate and/or magnesium hydroxide catalyst of the invention.

For best yields of the desired ortho-alkylated products, it is preferred to use at least one mole of the alkyl alcohol, and preferably from 1 to 3 moles, for each ortho position on the phenol to be alkylated. For example, if phenol, which has two ortho hydrogens per molecule, is to be methylated to produce a maximum yield of 2,6-xylenol, it is desirable to use two to six moles of methanol for each mole of phenol, with higher yields being obtained with higher ratios of methanol to phenol.

The vapors issuing from the reactor are condensed and the products are separated by conventional methods such as crystallization, distillation, etc. The reaction proceeds at atmospheric pressure, but pressures above or below can be used as desired.

The selectivity favoring ortho alkylation over meta or para alkylation of the phenol is good, and usually better than what is achievable with promoted or bound magnesium catalysts. Yields of 90% or greater are typical. These results are unexpected in view of prior art teachings which require promoters or polymeric binders for catalysts.

The invention is further illustrated by the examples which follow, which are not intended to be limiting.

PREPARATION OF CATALYST

A magnesium carbonate (MgCO₃) catalyst for use in the invention is prepared. For purposes of comparison, three ortho-alkylation catalysts in accordance with the prior art are also prepared. The procedures are described below.

MgCO3 catalyst (in accordance with invention)

About 225 grams of MgCO3, Merck Chemical Co. commercial grade, is thoroughly wet with distilled water by agitation in a beaker. The MgCO3 is then filtered on a fritted filter and the wet filter cake is dried in a pan in a vacuum oven. The dried cake is ground through a #25 mesh screen and 200 grams of this powder are put in a jar. Then 1.0 gram of graphite is added and the two powders are rolled on a jar mill for one hour to produce a 99.5:0.5 blend of MgCO3:graphite.

This blend is pre-compressed by tabletting on a Betapress and the tablets are ground using a mortar and pestle and sieved through the #25 mesh screen. The resulting denser powder is tabletted into the final tablets for use in the ortho-alkylating procedure.

MgCO3+MnOx (Comparison catalyst A)

This catalyst is made by first slurrying commercial grade MgCO3, Merck in distilled water. Then Mn(NO3)2, 50% commercial grade, is dropped into the slurry after dilution in distilled water. The ratio of MgCO3 to Mn(NO3)2, by weight, is 11.33/1, or 0.02 moles of Mn(NO3)2 per moles of MgCO3. This slurry is then stirred for four hours under nitrogen gas in a closed environment, at a temperature of 82° C.

After four hours the slurry is filtered and dried. The resulting powder, on analysis, is found to contain 1.0% Mn. Three hundred grams of the powder are blended with 1.5 grams of graphite by rolling on a jar mill for one hour. The 99.5/0.5 blend which results is tabletted on a Betapress. Precompression is necessary, so these first tablets are ground with a mortar and pestle and sieved through a #25 mesh screen. The resulting denser powder is tabletted into the final tablets for use in the ortho-alkylating procedure.

MgCO3+Polyphenylene ether (Comparison catalyst B)

Approximately 225 grams of MgCO3, Merck commercial grade, is first thoroughly wet with distilled water and then filtered on a fritted filter. The wet cake is dried in a vacuum oven and the dried cake is ground through a #25 mesh screen. 200 grams of this powder are put in a jar and 22.22 grams of poly(2,6-dimethyl-1,4-phenylene ether) (PPO, General Electric Co.) are added to this and the two powders are blended by rolling on the jar mill for 15 minutes. Thus, a 90:10 blend of MgCO3:PPO is created. Then 1.11 grams of graphite (Asbury A-99) are added to the jar and the three powders are rolled on the jar mill for one hour. This results in a 99.5:0.5 ratio of MgCO3+PPO:graphite. This blend is then precompressed, by tabletting, on the Betapress due to the lightness of the powder. The precompressed tablets are then ground with a mortar and pestle and sieved through the #25 screen. This denser powder is then tabletted into the final tablets for use in the ortho-alkylating procedure.

MgCO3+MnOx+Polyphenylene ether (Comparison catalyst C)

This catalyst is made by slurrying commercial grade MgCO3, Merck in distilled water. Then Mn(NO3)2, 50% commercial grade is dropped into the slurry after dilution in distilled water. The ratio of MgCO3 to Mn(NO3)2, by weight, is 11.3/1, or 0.02 moles of Mn(NO3)2 per mole of MgCO3. This slurry is stirred for four hours under a N2 blanket, in closed atmosphere, at a temperature of 82° C.

After four hours, the slurry is filtered and dried. This powder is determined to contain 1.0% Mn. 300 grams of this catalyst powder is then blended with 33.33 grams of PPO on the jar mill for 15 minutes to create a 90:10 blend of catalyst:PPO. Then 1.67 grams of graphite, Asbury A-99, are added to this and the powders are rolled on the jar mill for one hour to create a 99.5:0.5 blend of catalyst+PPO:graphite.

This blend is then precompressed on a Betapress. The tablets thus formed are ground with a mortar and pestle and sieved through the #25 screen. The denser powder thus obtained is then tabletted into the final tablets on the Betapress.

In the example, the reactor consists of two ¾ inch (I.D.) tubes. The feed, a solution of alcohol and phenol compound, is fed from a reservoir through a metering pump into the first of the two ¾ inch (I.D.) tubes which functions as a vertical vaporizer. The tube is 15 inches in length and is partially immersed to a depth of 8 inches in a fused salt bath. The vapors from the vaporizer are fed to the second ¾ inch (I.D.) tube, which functions as a vertical reactor, through a 2 inch length of stainless steel tubing located 5 inches above the bottom of the vaporizer and connected to the reactor tube 14 inches from its bottom. The reactor tube is 24 inches long and is immersed in the fused salt bath to a depth of 17 inches.

The inlet tube of the reactor coming from the vaporizer also passes through the fused salt bath and serves as a preheater for the vapor issuing from the vaporizer to bring the vapor up to the temperature of the reactor tube.

The second (reactor) ¾ inch (I.D.) tube is filled to a depth of 2 inches with glass beads which serve as support for the catalyst bed, and to a depth of 12 inches with 110 ml. of catalyst. The vapors from the vaporizer are fed to the top of the catalyst bed and product vapors leave the bottom of the reactor tube through a ⅜ inch (I.D.) stainless steel outlet tube. The product vapors are led to a water-cooled condenser and receiver where they are liquified and recovered.

EXAMPLE

A MgCO3 catalyst prepared as described above is evaluated in the reactor in a process according to the invention. After the reactor is charged with the catalyst and capped it is placed in a 370° C. salt bath and a stream of gaseous nitrogen at a rate of 2 standard cubic feet per hour is blown over the catalyst bed. After 15 minutes, the feed is started. The feed consists of 4/1 methanol/phenolics, with the phenolic being 60/40 phenol/ortho-cresol, and 20% water. The feed rate is 215 ml/hr., equivalent to a liquid having space velocity (LHSV) of 1.95 hr$^{-1}$. The LHSV defines the volume of liquid per volume of catalyst per hour. The rate is maintained for the duration of the run, 502 hours. The pressure is atmospheric.

Using the MgCO3 catalyst, a temperature program is followed to maintain the desired conversion. After the feed is established at 370° C., the temperature is raised to 445° C. which is reached, depending on the salt bath in use, in 1.5 to 2.5 hours. Listed below are the approximate time and temperature changes over the 502 hour run.

| Time, hours | Temp., °C. |
| --- | --- |
| 0 | 370 |
| 0.5–19 | 450 |

-continued

| Time, hours | Temp., °C. |
|---|---|
| 19–502 | 455 |

The results near the mid-point and at the end of the run are reported below:

| Phenolic Distribution | | | |
|---|---|---|---|
| Time, hours | Off gas, SCFH | Phenol, wt. % | o-cresol, wt. % |
| 196 | 0.5 | 0.8 | 13.2 |
| 502 | 0.3 | 1.6 | 18.1 |
| TWA | 0.4 | 1.7 | 18.5 |
| Time, hours | 2,6-xylenol produced, wt. % | 2,4,6-trimethylphenol produced, wt. % | |
| 196 | 80.4 | 5.3 | |
| 502 | 75.5 | 4.5 | |
| TWA | 73.7 | 5.5 | |

For purposes of comparison, the same procedure is repeated, except that the MgCO₃ catalyst is substituted with comparison catalysts A (MgCO₃+MnOx), B (MgCO₃+PPO) and C (MgCO₃+MnOx+PPO), respectively. The phenolic distribution data for each are given below.

| Catalyst A (MgCO₃ + MnOx) | | | |
|---|---|---|---|
| Time, hrs. | Off gas, SCFH | Phenol, wt. % | o-Cresol, wt. % |
| 196 | 0.6 | 1.0 | 14.1 |
| 502 | 0.5 | 2.6 | 19.7 |
| TWA | 0.5 | 1.7 | 16.9 |
| Time, hrs. | 2,6-xylenol produced, wt. % | 2,4,6-trimethylolphenol produced, wt. % | |
| 196 | 77.6 | 6.9 | |
| 502 | 71.9 | 5.5 | |
| TWA | 73.2 | 7.5 | |

| Catalyst B (MgCO₃ + PPO) | | | |
|---|---|---|---|
| Time, hrs | Off gas, SCFH | Phenol, wt. % | o-Cresol, wt. % |
| 196 | 0.5 | 1.2 | 15.3 |
| 502 | 0.4 | 1.9 | 17.6 |
| TWA | 0.4 | 1.9 | 18.1 |
| Time, hrs | 2,6-xylenol produced, wt. % | 2,4,6-trimethylphenol produced, wt. % | |
| 196 | 77.7 | 5.5 | |
| 502 | 75.5 | 4.7 | |
| TWA | 73.3 | 6.0 | |

| Catalyst C (MgCO₃ + MnOx + PPO) | | | |
|---|---|---|---|
| Time, hrs. | Off gas, SCFH | Phenol, wt. % | o-Cresol, wt. % |
| 196 | 0.6 | 2.8 | 20.2 |
| 502 | 0.4 | 6.3 | 25.4 |
| TWA | 0.5 | 4.5 | 23.8 |
| Time, hrs. | 2-6-xylenol produced, wt. % | 2,4,2-trimethylphenol, wt. % | |
| 196 | 70.4 | 6.2 | |
| 502 | 63.2 | 4.8 | |
| TWA | 64.5 | 6.5 | |

| The overall results are summarized as follows: | | | | |
|---|---|---|---|---|
| Run # | 1 | 2 | 3 | 4 |
| catalyst | MgCO₃ | MgCO₃ + MnOx | MgCO₃ + PPO | MgCO₃ + MnOx + PPO |
| wt. % 2,6 | 73.7 | 73.2 | 73.3 | 64.5 |
| wt. % 2,4,6 | 5.5 | 7.5 | 6.0 | 6.5 |
| Off gas SCFH | 0.4 | 0.5 | 0.4 | 0.5 |
| Selectivity ratio | 13.4 | 9.8 | 12.2 | 9.7 |

It can be seen that run #1, using MgCO₃ catalyst above in accordance with the invention, produces superior results. The above data indicates that MnOx (run #2) is primarily responsible for increased off gas and decreased selectivity, both of which are undesirable. PPO (run #3) contributes slightly to decreased selectivity, probably due to a porosity effect. The use of both MnOx and PPO (run #4) is also inferior—run #1 results in 14% higher conversion, 16% lower off gas and 35% higher selectivity by comparison.

The above-mentioned patents and/or publications are incorporated herein by reference. Obviously, other modifications and variations of the invention are possible in the light of the above disclosure. For instance, instead of magnesium carbonate (MgCO₃), "basic" magnesium carbonate, magnesium hydroxide or a mixture of magnesium carbonate and magnesium hydroxide can be used as the catalyst. It is, therefore, to be understood that changes may be made in the particular embodiments of the invention described which are within the full intended scope of the invention as described in the appended claims.

We claim:

1. In a process for alkylating a phenolic compound in the ortho position which comprises the vapor phase reaction in the presence of an alkylation catalyst of an alkylation feed mixture comprising an alkyl alcohol having up to about 16 carbon atoms and a phenolic compound having at least one ortho hydrogen, the phenolic compound represented by the formula

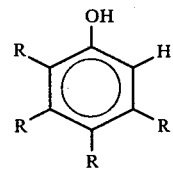

wherein R is a monovalent substituent selected from the group consisting of hydrogen, alkyl, phenyl and alkyl substituted phenyl, the improvement comprising conducting the reaction in the presence of a catalyst consisting of a calcination residue derived from heating a magnesium-containing compound wherein said heating which provides a calcination residue takes place in the presence of said alkylation feed mixture in situ in a reactor.

2. A process according to claim 1, in which the reaction is conducted at a temperature in the range of 400°–460° C.

3. A process according to claim 1, in which the catalyst is magnesium carbonate.

4. A process according to claim 1, in which the magnesium carbonate is in the form of "basic" magnesium carbonate.

5. A process according to claim 1, in which the reaction is run above atmospheric pressure.

6. A process according to claim 1, in which the catalyst is magnesium hydroxide.

7. A process according to claim 1, in which the catalyst is a mixture of magnesium carbonate and magnesium hydroxide.

8. A process according to claim 7, in which the magnesium carbonate is in the form of "basic" magnesium carbonate.

9. A process according to claim 1, where the process is carried out in the presence of water.

10. A process according to claim 1, in which the alcohol is methyl alcohol.

11. A process according to claim 1, in which the phenolic compound is phenol.

12. A process according to claim 1, in which the phenolic compound is o-cresol.

13. A process according to claim 1, in which the phenolic compound is a mixture of phenol and o-cresol.

14. The process of claim 1 wherein said magnesium-containing compound is magnesium carbonate, or magnesium hydroxide, or a mixture of magnesium carbonate and magnesium hydroxide.

15. The process of claim 1 wherein said feed mixture contains at least one mole of alkyl alcohol for each ortho position on the phenolic compound to be alkylated.

16. The process of claim 1 wherein said feed mixture comprises methanol and phenolic compounds provided by a mixture of phenol and o-cresol, said feed mixture having from about two to about six moles of methanol for each mole of phenolic compound, with phenol constituting at least about 50 mole percent of the phenolic compounds.

17. The process of claim 1 wherein said feed mixture comprises methanol and phenol, said feed mixture having about two to about six moles of methanol per mole of phenol.

18. The process of claim 16 or wherein said feed mixture further comprises water.

19. The process of claim 1 wherein said heating of magnesium carbonate, magnesium hydroxide, or a mixture of the two, takes place at a temperature in a range from about 400° to about 460° C.

20. In a process for preparing 2,6-xylenol by reacting in the vapor phase, in the presence of an alkylation catalyst, methanol and a mixture of phenol and o-cresol, the improvement comprising conducting the reaction in the presence of a calcination residue derived by heating magnesium carbonate at a temperature in the range 400°–460° C. in the presence of an alkylation feed mixture comprising methanol and a mixture of phenol and o-cresol and in situ in a reactor.

21. A process according to claim 20, where the process is carried out in the presence of water.

22. The process of claim 20 wherein said feed mixture comprises from about 60 to about 90 mole percent methanol, from about 8 to about 20 mole percent phenol, and from about 5 to about 15 mole percent o-cresol.

23. The process of claim 20 wherein said feed mixture comprises about 4 moles of methanol, about 0.6 mole phenol and about 0.4 mole o-cresol.

24. The process of claim 20 wherein the liquid hourly space velocity is in a range from about 0.5 $hr^{-1}$ to about 4.0 $hr^{-1}$.

* * * * *